United States Patent [19]

Raines

[11] Patent Number: 4,627,843

[45] Date of Patent: Dec. 9, 1986

[54] GUARD FOR RIGHT ANGLE INFUSION NEEDLE

[75] Inventor: Kenneth C. Raines, Bethlehem, Pa.

[73] Assignee: Burron Medical Inc., Bethlehem, Pa.

[21] Appl. No.: 780,310

[22] Filed: Sep. 26, 1985

Related U.S. Application Data

[63] Continuation-in-part of Ser. No. 747,569, Jun. 24, 1985.

[51] Int. Cl.⁴ .............................................. A61M 5/32
[52] U.S. Cl. .................................... 604/263; 604/192
[58] Field of Search ............... 604/263, 192, 197, 198, 604/162, 174, 177, 240, 180

[56] References Cited

U.S. PATENT DOCUMENTS

| | | | |
|---|---|---|---|
| 3,324,853 | 6/1967 | Czorny et al. | 604/162 |
| 3,658,061 | 4/1972 | Hall | 604/263 |
| 3,901,226 | 8/1975 | Scardenzan | 604/263 |
| 4,250,880 | 2/1981 | Gordon | 604/180 |
| 4,500,312 | 2/1985 | McFarlane | 604/263 |

Primary Examiner—Stephen C. Pellegrino
Assistant Examiner—John D. Ferros
Attorney, Agent, or Firm—Shoemaker and Mattare, Ltd.

[57] ABSTRACT

A guard for a right angle winged infusion needle includes an elongated trough-like body which receives and protects the needle and an end socket extension which receives and holds a finger pad bonded to the wing at one end of the needle and disposed in a plane perpendicular to the needle.

8 Claims, 5 Drawing Figures

U.S. Patent Dec. 9, 1986 4,627,843
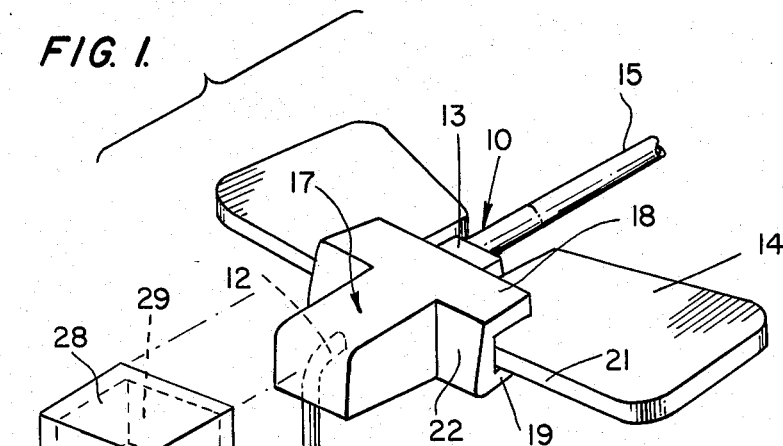
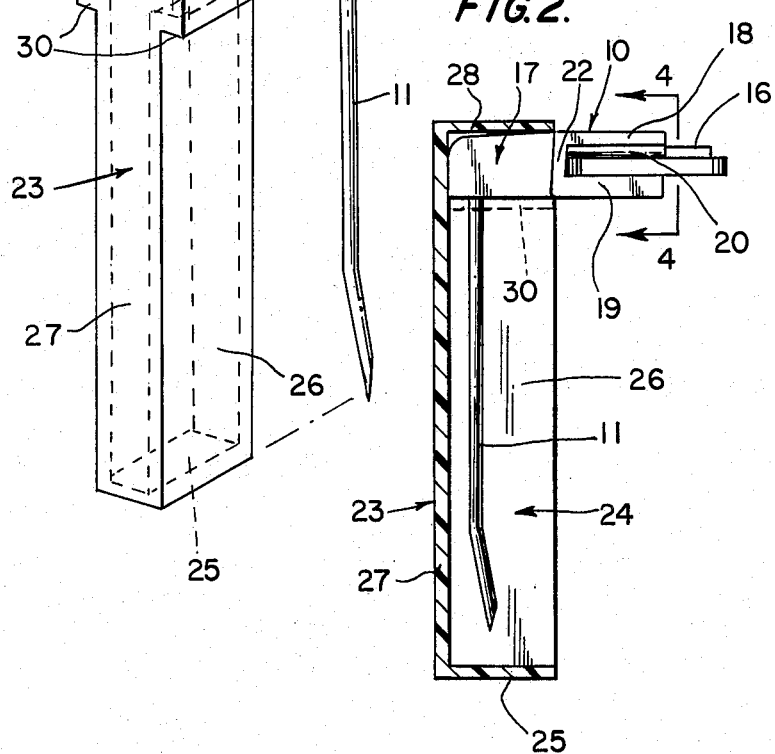
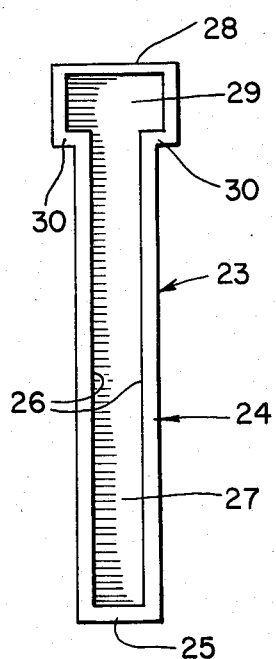
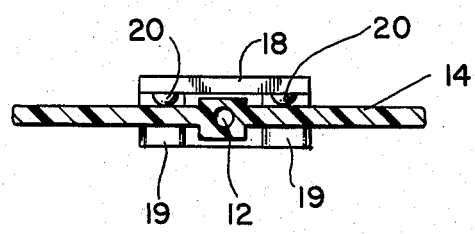
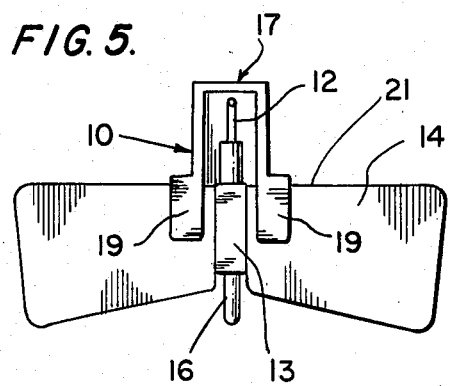

GUARD FOR RIGHT ANGLE INFUSION NEEDLE

CROSS-REFERENCE TO RELATED APPLICATION

This application is a continuation-in-part of prior copending application Ser. No. 747,569, filed June 24, 1985, for GUARD FOR RIGHT ANGLE WINGED INFUSION NEEDLE.

BACKGROUND OF THE INVENTION

The present invention relates to a unitary, simplified and inexpensive guard for a winged right angle infusion needle of the general character disclosed in the above-referenced prior patent application.

The guard in the prior patent application included an elongated trough-like body to receive and protect the infusion needle, and an integral somewhat resilient clip extension at one end of the trough-like body adapted to grip the center hub portion of the infusion needle wing attachment. The clip extension projects beyond the open side of the trough body portion of the guard in the prior application.

The present application discloses a guard for a right angle winged infusion needle of the type having a finger pad connected with the somewhat flexible wing. The arrangement is such that the user of the needle can apply pressure on the finger pad with the index finger while holding the ends of the flexible wing between the thumb and middle finger, as when inserting the needle into body tissue or into an implantable venous access device. This arrangement also provides for a low profile device that is easy to insert and mechanically stable when taped in position.

The guard, according to the present invention, is even more simplified than the guard in the prior application inasmuch as a socket extension for receiving and holding the needle finger pad is flush with the open side of the trough-like body of the guard, and no parts of the guard project laterally thereof. This simplified guard structure is advantageous in the manufacturing and packaging of the product.

Other features and advantages of the invention will become apparent to those skilled in the art during the course of the following detailed description.

BRIEF DESCRIPTION OF THE DRAWINGS

FIG. 1 is an exploded perspective view showing a guard for a right angle winged infusion needle according to the present invention.

FIG. 2 is a central vertical longitudinal section taken through the guard with the infusion needle being held therein.

FIG. 3 is a side elevation of the guard looking toward the open side thereof.

FIG. 4 is an enlarged vertical section taken on line 4—4 of FIG. 2.

FIG. 5 is a bottom plan view showing the wing and finger pad attachment for the right angle infusion needle.

DETAILED DESCRIPTION

Referring to the drawings in detail wherein like numerals designate like parts, a right angle infusion needle 10 includes a needle shank 11 requiring protection and a right angle extension 12 at one end of the shank 11 received through the hub portion 13 of a somewhat flexible wing attachment 14. A suitable flexible infusion tube 15, FIG. 1, is connected with and extends from the hub portion 13, which may be equipped with a nipple 16, FIG. 5, over which one end of the tube 15 may be telescoped.

The infusion needle 10 also includes a finger pad 17 having a rear upper flange 18 and laterally spaced lower side fingers 19. The lower face of the flange 18 is preferably equipped with a pair of spaced ribs 20. The portion of the finger pad 17 which projects forwardly of the flange 18 and fingers 19 is generally rectangular, hollow and open on its lower side to accommodate the needle extension 12, as best shown in FIG. 5.

In the manufacturing process for the infusion needle, the wing 14 is inserted between the flange 18 and fingers 19 which grippingly engage the wing. The hub portion 13 of the wing is received between the fingers 19, and the front edge 21 of the wing 14 abuts a front wall 22 between flange 18 and fingers 19. Preferably, the wing 14 is bonded in assembled relationship with the finger pad 17.

A guard 23 for the right angle infusion needle comprises the main subject matter of the present invention. The guard 23 is unitary and adapted to be molded from plastics material. It could, however, be fabricated from a different material.

The guard or protector 23 comprises an elongated rectangular trough-like body 24 open along one side. The trough-like body 24 includes one end wall 25, two spaced side walls 26, and one longitudinal wall 27, all integrally connected. The trough-like body 24 of the guard 23 is sized to receive therein and protect the shank 11 of the right angle infusion needle, as shown in FIG. 2.

The trough-like body portion 24 is open at its end away from the end wall 25, and is provided at this end with a laterally enlarged rectangular socket extension 28 or head, adapted to receive therein the portion of the finger pad 17 which extends beyond the flange 18 and wall 22, FIG. 2. Preferably, the finger pad 17 has a snug fit within the socket extension 28 so that the infusion needle 10 will remain assembled with the guard 23 until forcibly removed.

The socket opening 29 of the socket extension 28 is rectangular and matches the shape of the portion of the finger pad 17 which it receives. The socket opening 29 communicates with the interior of the elongated trough-like body 24, FIG. 3. A pair of shoulders 30 project outwardly laterally from the side wall 26 of the body 24 equidistantly, FIG. 3. The open side of the socket extension 28 lies in a common plane with the open side of the trough-like body 24, whereby no part of the guard projects outwardly of its open side. The construction of the guard 23 is simplified and the guard is very easy to store and package. The major axes of the trough-like body portion 24 and socket extension 28 are disposed at right angles.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A guard for a right angle infusion needle having a wing and finger pad attachment comprising an elongated trough-like body portion having an open side and being adapted to receive and protect the shank of the infusion needle, and a socket extension on one end of the trough-like body portion and extending at right angles to said body portion, said socket extension having a cross-sectional shape corresponding to the shape of a part of said wing and finger pad attachment and receiving said part to releasably hold the infusion needle assembled with said guard.

2. A guard for a right angle infusion needle as defined in claim 1, and said socket extension having an open side lying in a common plane with the open side of the trough-like body portion, the interiors of the body portion and socket extension being in communication.

3. A guard for a right angle infusion needle as defined in claim 2, and said socket extension being somewhat wider than the trough-like body portion across the longitudinal axis of the body portion to accommodate said part of the wing and finger pad attachment which is wider than the interior of said body portion.

4. A guard for a right angle infusion needle as defined in claim 3, and the socket extension being rectangular and being connected with the side walls of said body portion by a pair of lateral shoulders having equal lengths.

5. A guard for a right angle infusion needle as defined in claim 4, and the trough-like body portion and socket extension sharing a common back wall disposed in one plane which is parallel to the open sides of the body portion and socket extension.

6. A unitary guard for a right angle infusion needle comprising an elongated trough-like body portion having an open side to receive a shank of the needle, and a laterally enlarged socket extension on one end of the trough-like body portion and extending at right angles to said body portion and communicating with the interior thereof, said socket extension having a shape corresponding to the shape of a portion of a wing and finger pad attachment on the infusion needle and receiving said portion releasably.

7. A unitary guard for a right angle infusion needle as defined in claim 6, and the laterally enlarged socket extension having a pair of support shoulders for said portion of the wing and finger pad attachment and said shoulders being joined to opposite longitudinal side walls of the trough-like body portion substantially at right angles thereto.

8. A unitary guard for a right angle infusion needle as defined in claim 7, and said trough-like body portion and socket extension having open sides in a common plane and having a common back wall in one plane which is parallel to said common plane.

* * * * *